Figure 1:
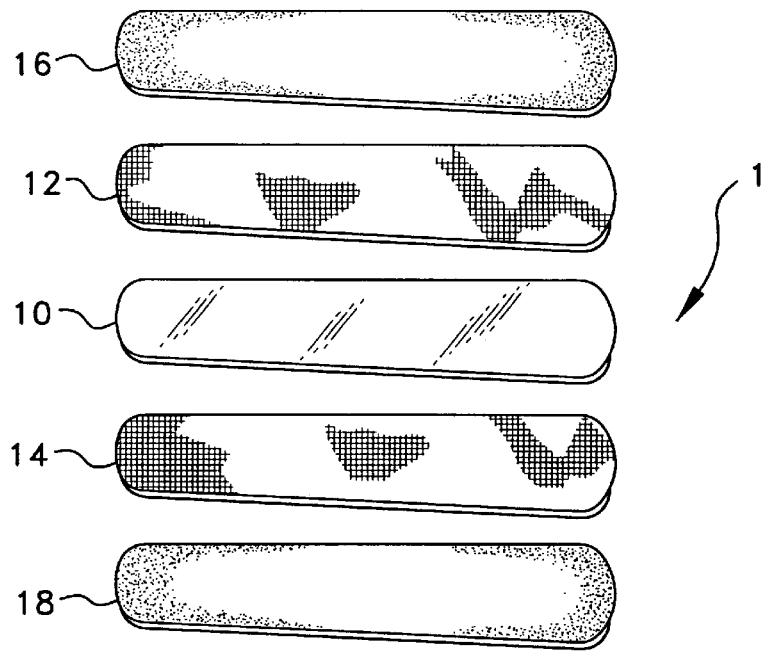

United States Patent [19]
Reinbold et al.

[11] Patent Number: 6,033,370
[45] Date of Patent: *Mar. 7, 2000

[54] CAPACITATIVE SENSOR

[75] Inventors: Kirk A. Reinbold, Phoenixville; Robert J. Goldman, Philadelphia, both of Pa.

[73] Assignee: Preventive Medical Technologies, Inc., Phoenixvill, Pa.

[*] Notice: This patent is subject to a terminal disclaimer.

[21] Appl. No.: 08/982,918

[22] Filed: Dec. 2, 1997

Related U.S. Application Data

[63] Continuation-in-part of application No. 08/467,744, Jun. 6, 1995, Pat. No. 5,775,332, which is a continuation of application No. 07/908,121, Jul. 1, 1992, Pat. No. 5,449,002.

[51] Int. Cl.[7] .................................................. A61B 5/103
[52] U.S. Cl. ......................... 600/595; 600/587; 600/592; 361/291
[58] Field of Search ................................... 600/587, 592, 600/595; 73/172, 379.02, 379.01, 379.04; 361/290, 291

[56] References Cited

U.S. PATENT DOCUMENTS

| | | | |
|---|---|---|---|
| 4,595,023 | 6/1986 | Bonnet | 600/595 |
| 5,226,650 | 7/1993 | Suttner | 273/73 |
| 5,439,477 | 8/1995 | McEwen | 606/203 |
| 5,449,002 | 9/1995 | Goldman | 128/779 |
| 5,605,336 | 2/1997 | Gaoiran et al. | 273/445 |
| 5,608,599 | 3/1997 | Goldman | 361/283.1 |
| 5,662,123 | 9/1997 | Goldman | 600/595 |
| 5,681,993 | 10/1997 | Heitman | 73/379.02 |
| 5,723,786 | 3/1998 | Klapman | 482/84 |
| 5,775,332 | 7/1998 | Goldman | 128/774 |

*Primary Examiner*—Cary O'Connor
*Assistant Examiner*—Charles Marmor, II
*Attorney, Agent, or Firm*—Duane, Morris & Heckscher LLP

[57] ABSTRACT

A capacitive force sensor which has a plurality of layers forming a force sensing detector, the detector providing a signal in response to pressure, feedback output in response to the signal from the force sensing detector and a housing for encompassing the force sensing detector and the feedback providing element. The housing can be a squeeze ball, squeeze cylinder, a hitting target, a baseball or golf glove or can be implemented as part of an actual grip, such as for a golf club.

41 Claims, 16 Drawing Sheets

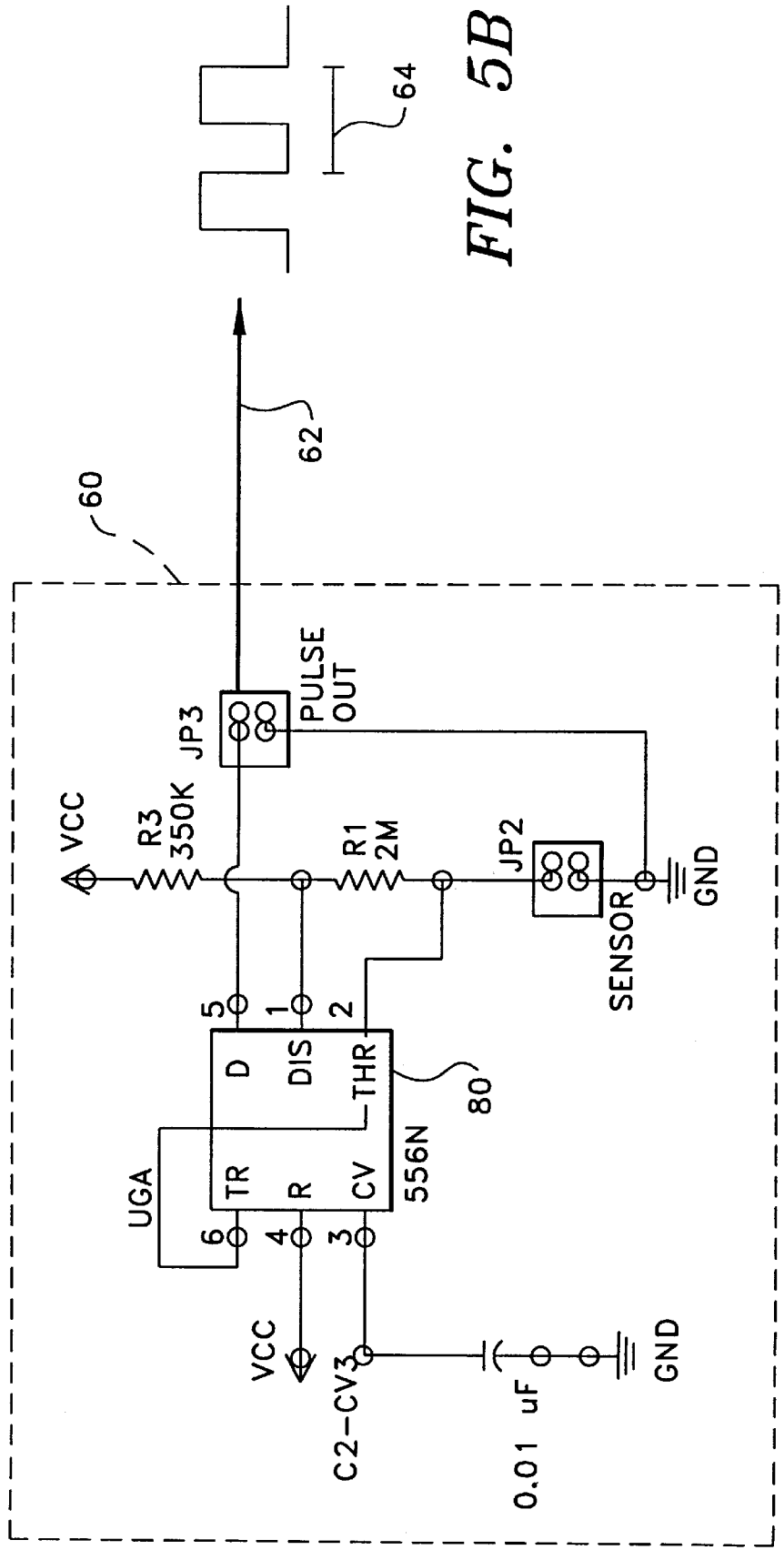

CAPACITATIVE SENSOR

RELATED APPLICATIONS

This application is a continuation-in-part of U.S. patent application Ser. No. 08/467,744 filed Jun. 6, 1995, now U.S. Pat. No. 5,775,332 which is a continuation of U.S. application Ser. No. 908,121, and filed Jul. 1, 1992, now U.S. Pat. No. 5,449,002, issued Sep. 12, 1995.

FIELD OF THE INVENTION

This invention relates to a capacitive sensor which provides feedback to the user. More specifically, this invention relates to a multi-layer capacitive sensor adaptable to a variety of recreational devices which provides user feedback in response to pressure or force exerted by the user.

BACKGROUND OF THE INVENTION

In the United States, approximately 5000–6000 toy industry products are introduced each year, most of which are created by research and development specialists at the more than 800 toy manufacturers based in the United States. Toy industry retail sales in 1996 rose to an estimated $20.7 billion, up from $20 billion in 1995. Manufacturers shipments totaled $13.94 billion in 1996 versus $13.45 billion in 1995. Of the major product categories, the strongest performers were dolls, up 12 percent, ride-ons up 10.4 percent and games/puzzles, which registered a 7.5 percent increase. Annual retail sales estimates are based upon a constant gross profit of about 33 percent and do not include video hardware and software sales.

Many of the toys which garner the most attention reflect the latest technological advances or are innovative extensions of basic products. Along with providing opportunities for fun and learning, toys traditionally mirror scientific progress, changes in social attitudes and topical customs and values from the adult world.

At the earliest stages, many toy designers utilize information from sources including parents, psychologists, educators and other child development specialists. This background provides valuable clues as to what consumers are looking for when they purchase toys. Toys also are frequently tested by the children themselves in focus groups or at home to determine durability, age appropriateness, play patterns and marketability. A number of toy manufacturers maintain in-house, year round nursery school facilities for this purpose, while others establish relationships with universities and other research facilities.

Many factors influence the success of a given toy or product line, including perceived value, multiple play possibilities, eye catching design, innovative line extensions, creative marketing, proper in-store exposure, reasonable availability, and positive "word of mouth", i.e., child-to-child, parent-to-parent. However, one characteristic that is present in most of the toys that prove to be best sellers, is interactivity. Interactivity is basically the toys' ability to respond and provide a response to input or action by the user. While less mature or younger children are content to play with inert toys such as blocks and teddy bears, more developed children are searching for something more, in the form of a toy which can provide some response to their actions.

While the majority of adults outgrow the use and enjoyment of toys after their teenage years, they still seek out devices and products which can provide stimulating and gratifying enjoyment. This sector of the marketplace is often occupied by sport related or therapeutical products. For example, a myriad of exercise machines exist today, ranging all the way from a simple grip strengthener all the way to complex ten-station workout machines. Again, while the more inert products such as a simple punching bag are popular, the devices which can provide the user with instantaneous and instant feedback are the most popular. Recent trends for modern products incorporate the use of devices such as performance monitors and vital sign readouts for heart rate, blood pressure, etc. Thereby, it would be desirable to have a product which can provide both children and adults with instant gratification in the form of a responsive toy or recreational device. It would be further desirable if this product could be implemented in a variety of existing devices to make them more interactive in nature.

SUMMARY OF THE INVENTION

A moldable capacitive force sensor (or force transducer) comprising a plurality of layers forming a force sensing detector, the detector providing an output signal in response to pressure, means for providing feedback in response to the output signal from the force sensing detector and housing means for encompassing the force sensing detector and the feedback providing means. The sensor is moldable in the sense that it is flexible, elastic or otherwise pliable so that it can conform to a variety of geometries dependent upon the particular application. The housing means can be a squeeze ball, squeeze cylinder, a hitting target, a baseball glove or can be implemented as part of a grip, such as for a golf club.

The capacitive transducer consists of an open cell polyurethane foam dielectric sandwiched between two conductor layers. Two end plates enclose the sandwiched layers. Two end plates that act as insulation can fully enclose the sandwiched layers. The capacitive transducer can also be implemented in a three layer configuration. In this embodiment, the transducer is comprised of foam dielectric layers surrounded by a plurality of conductor layers. As in the two layer construction, two end plates fully enclose the sandwiched layers.

A BRIEF DESCRIPTION OF THE DRAWINGS

Figure 2A:
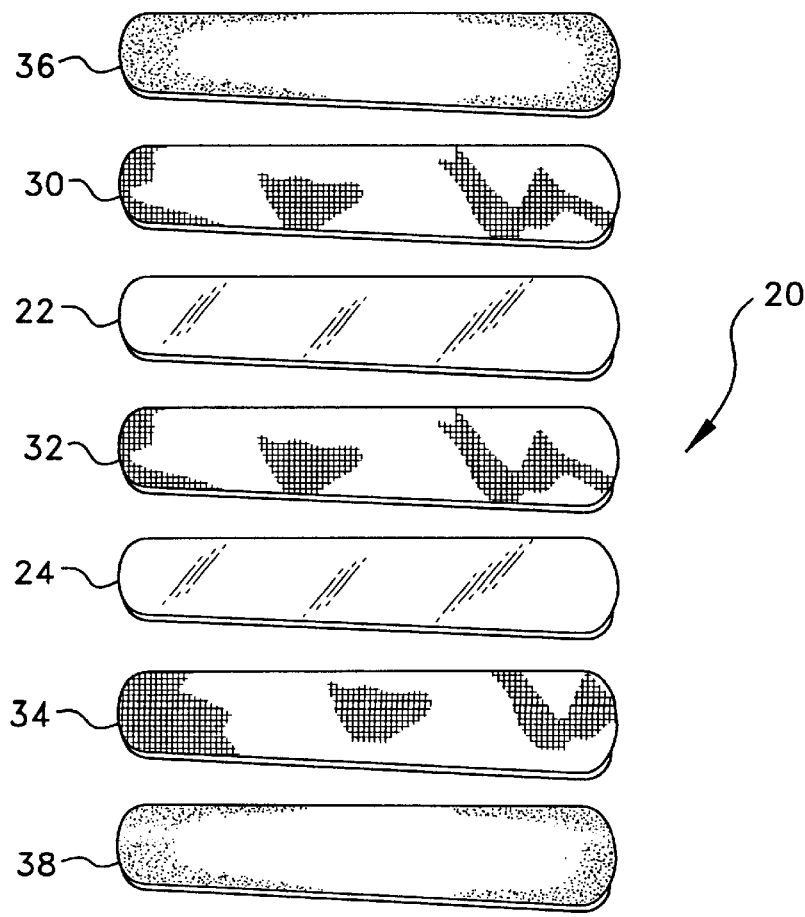
Figure 2B:
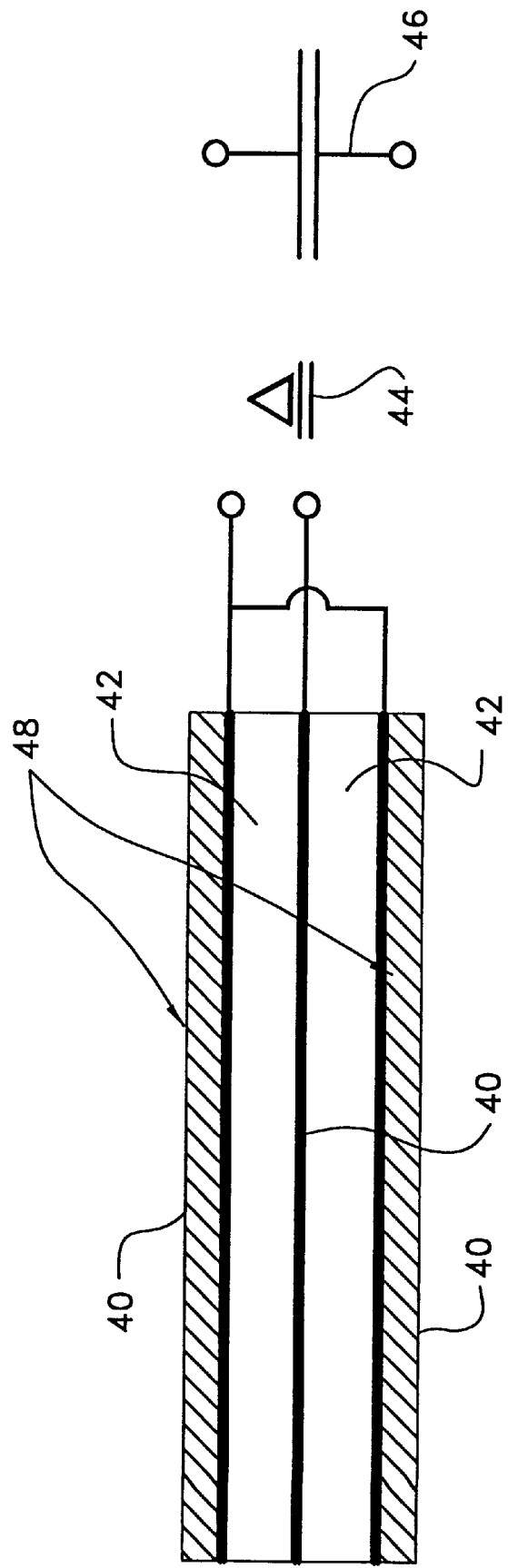
Figure 3:
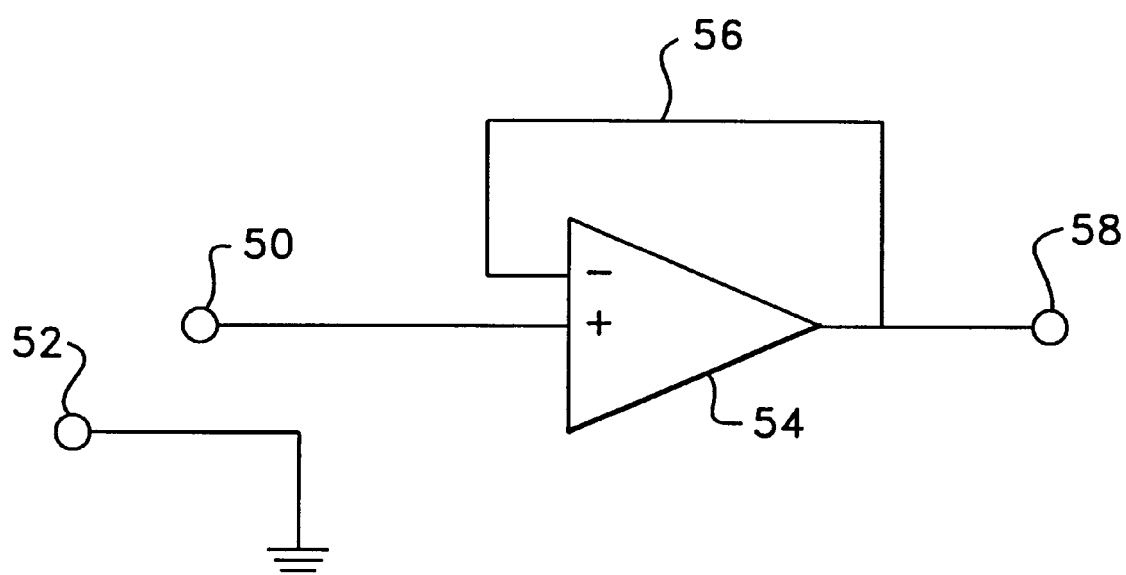
Figures 4A, 4B:
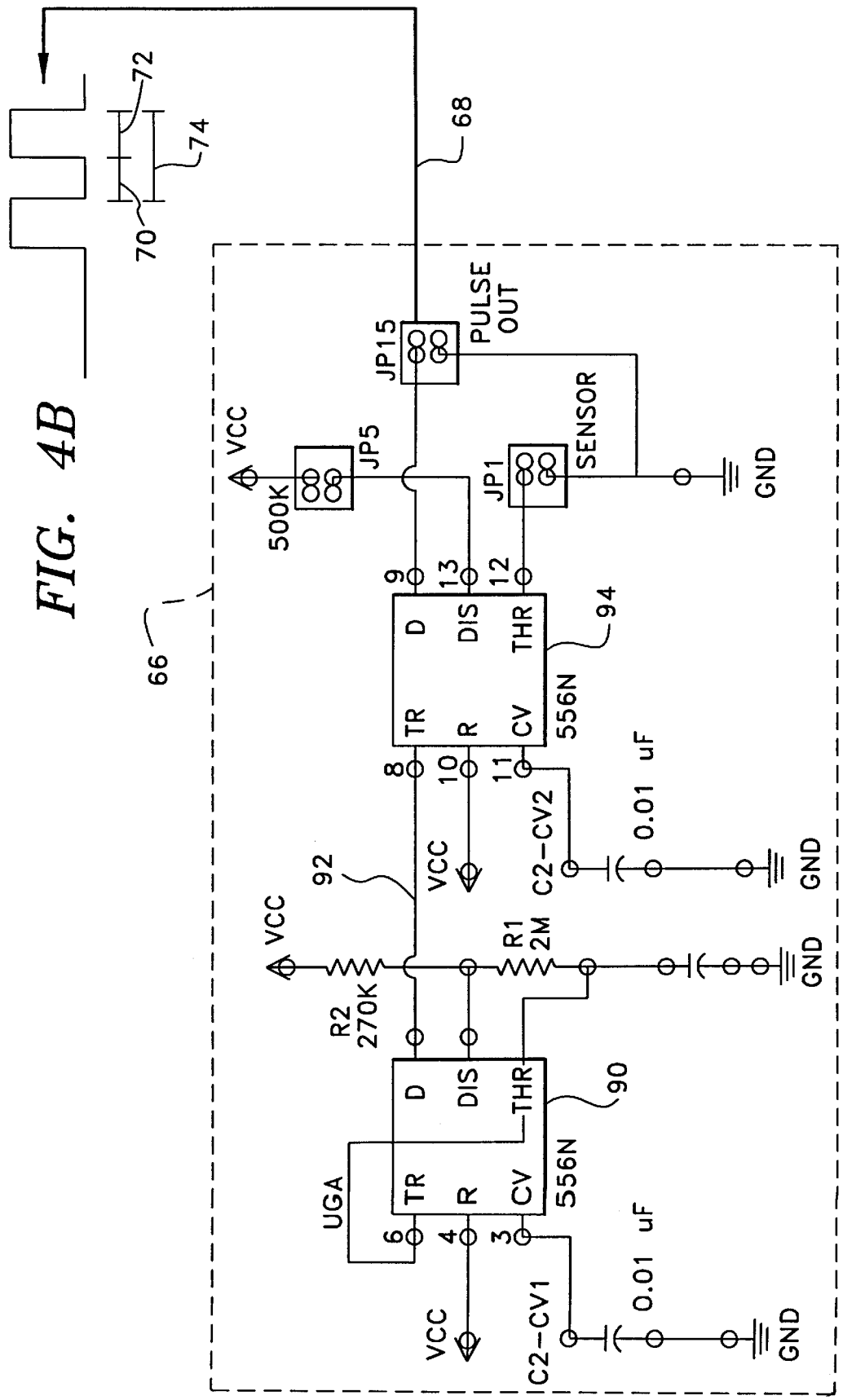
Figure 6A:
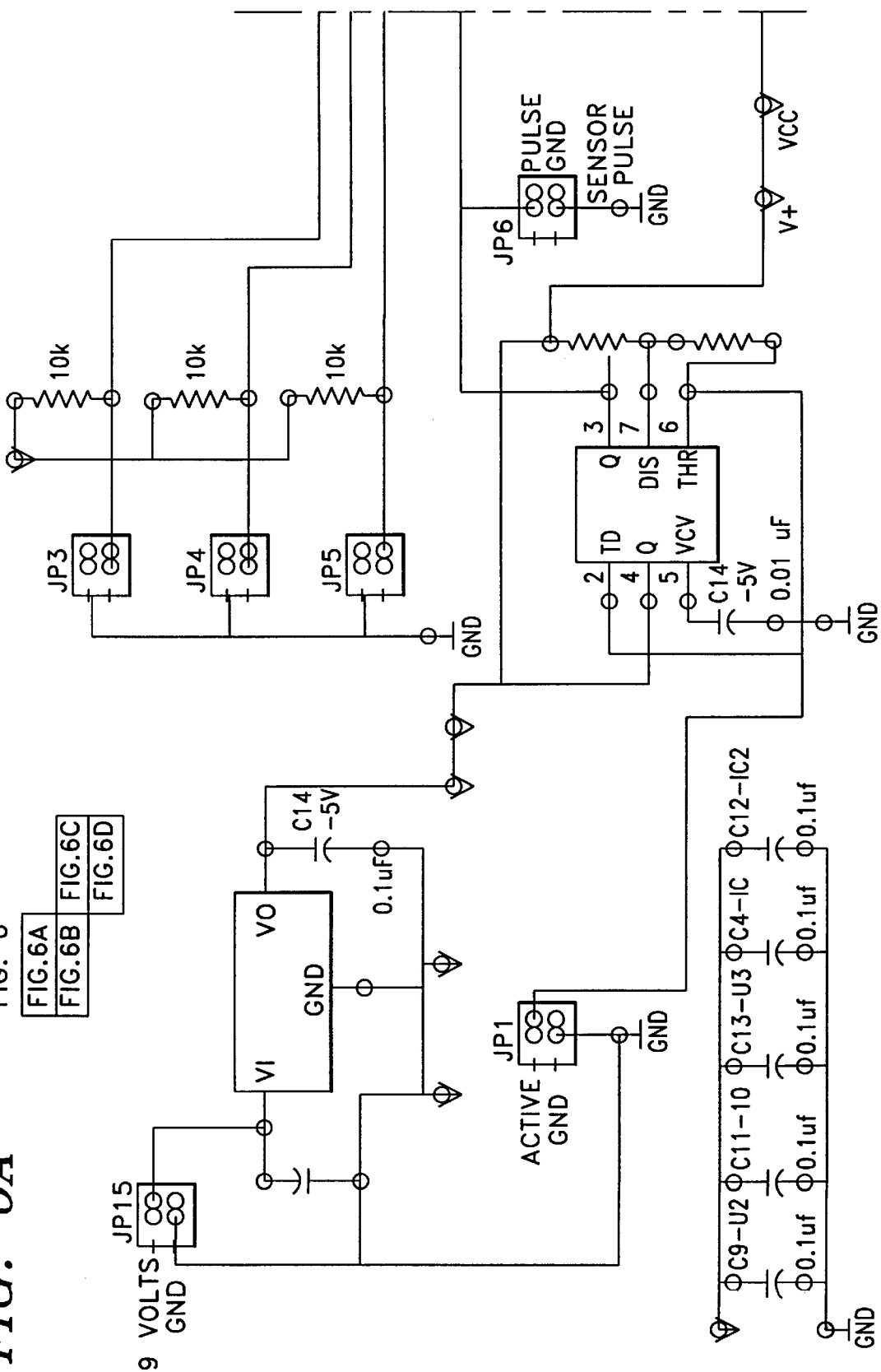
Figure 6B:
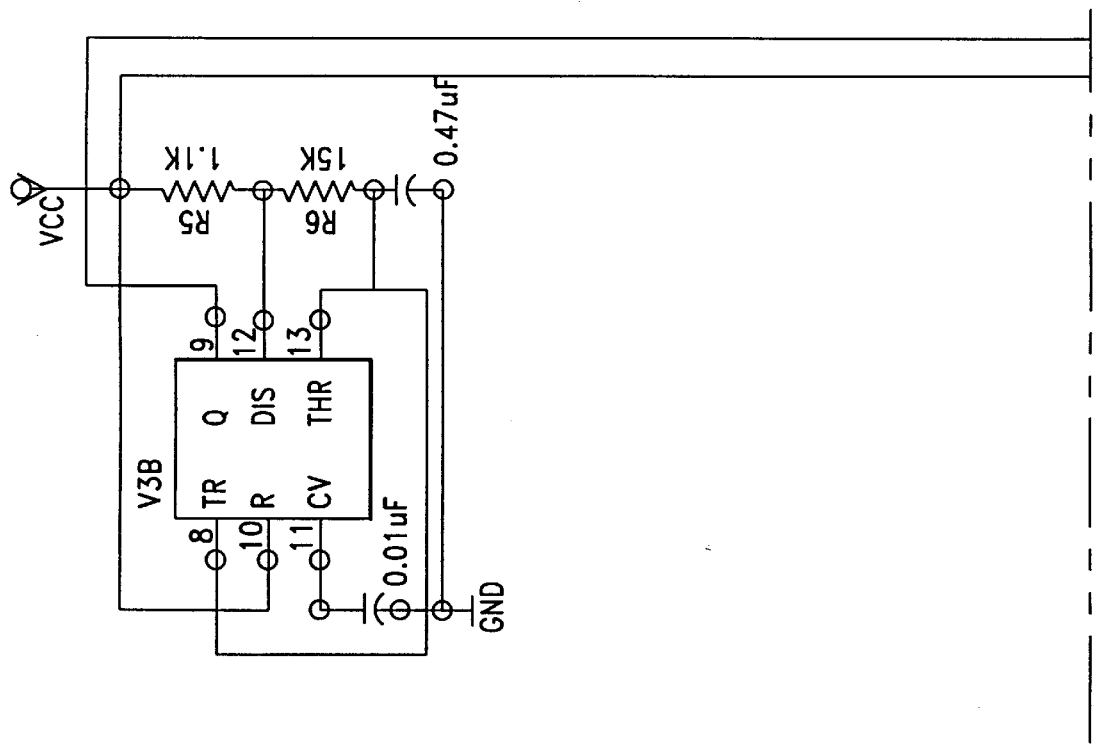
Figure 6C:
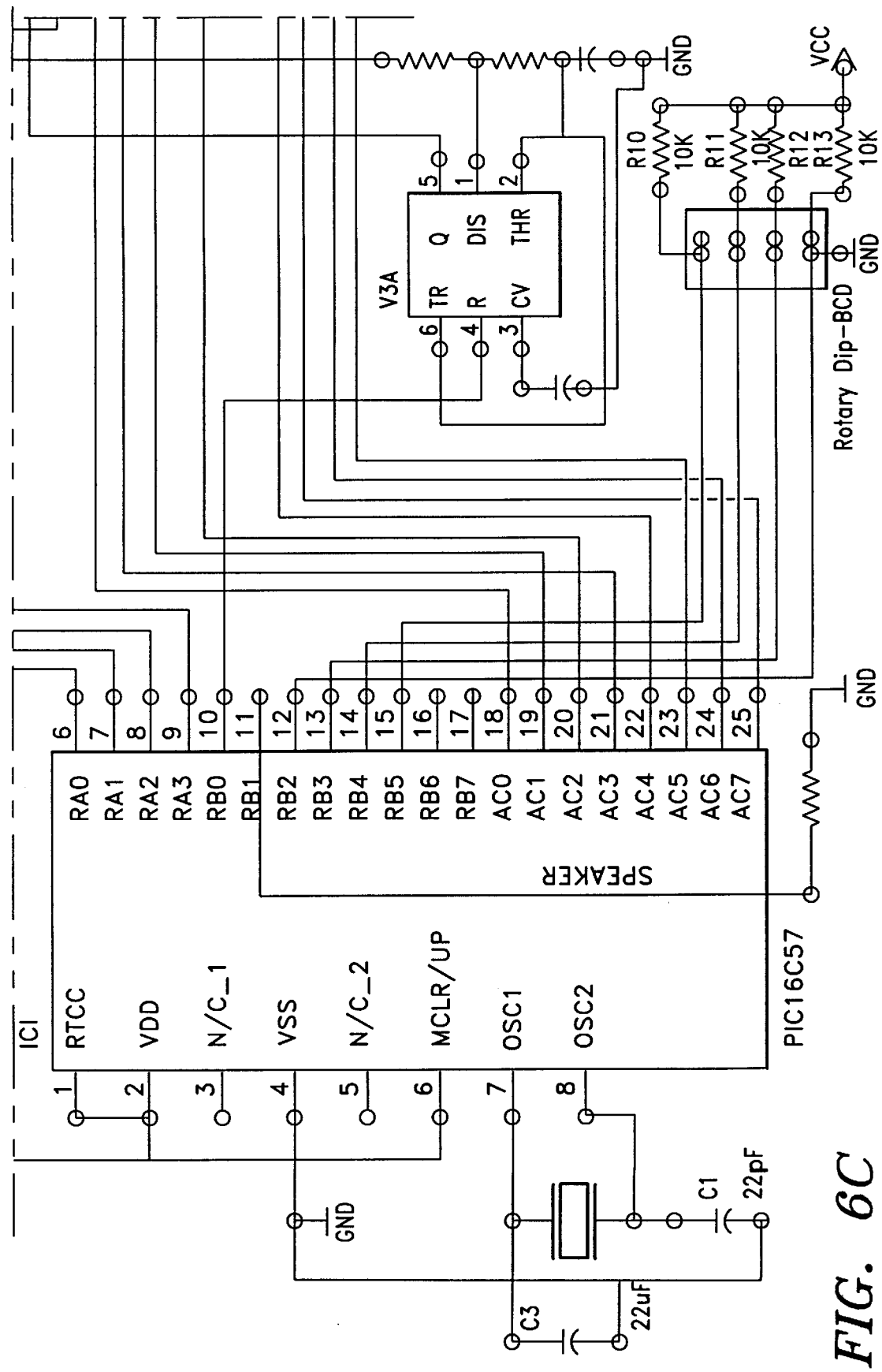
Figure 6D:
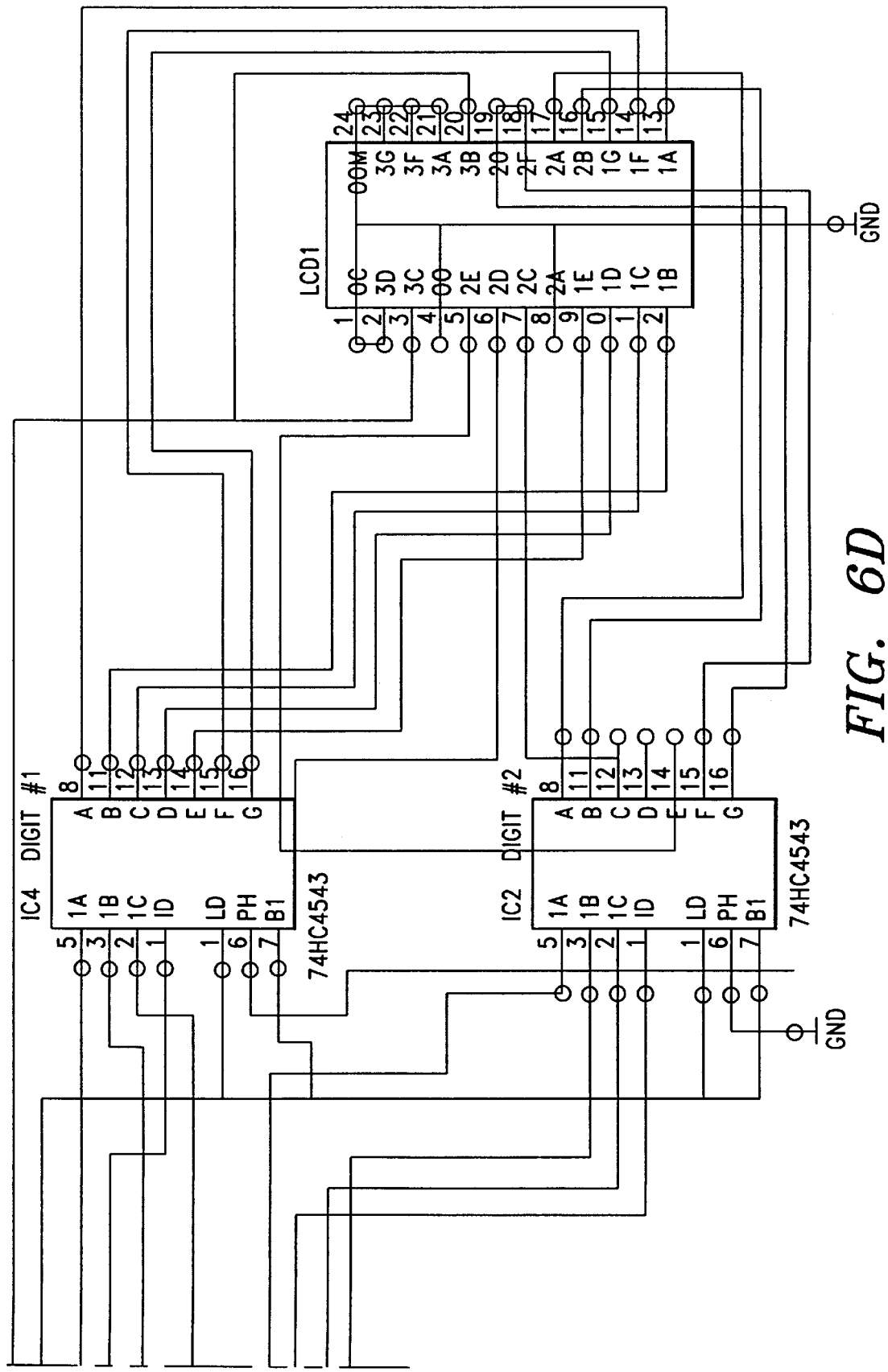
Figure 7:
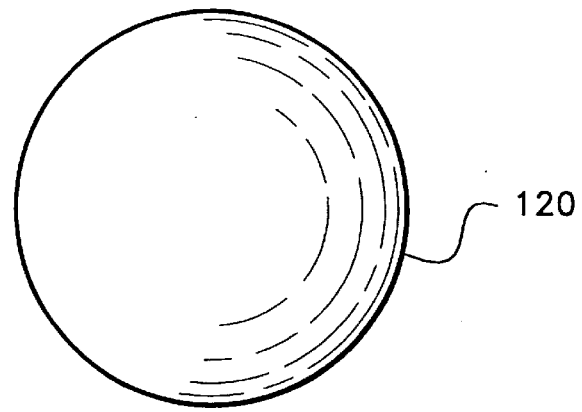
Figure 8:
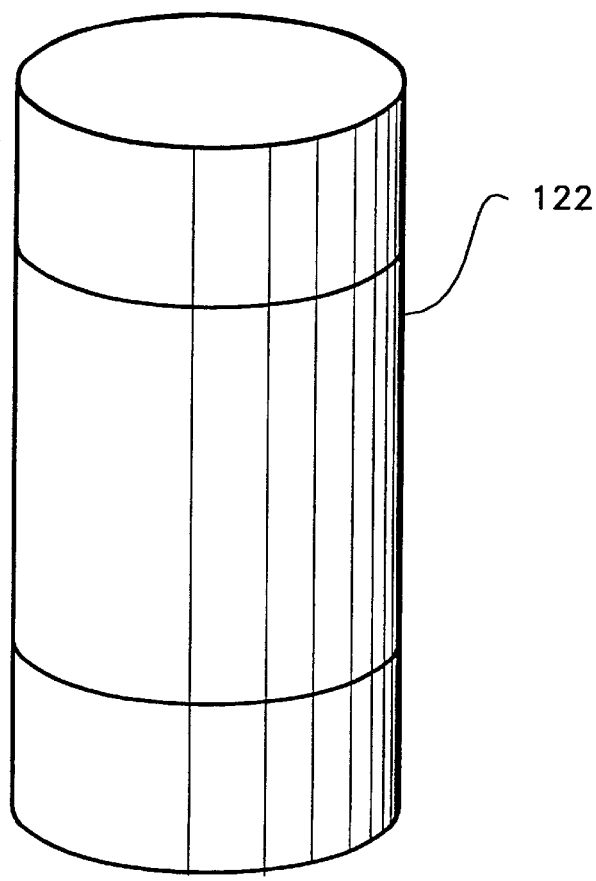
Figure 9:
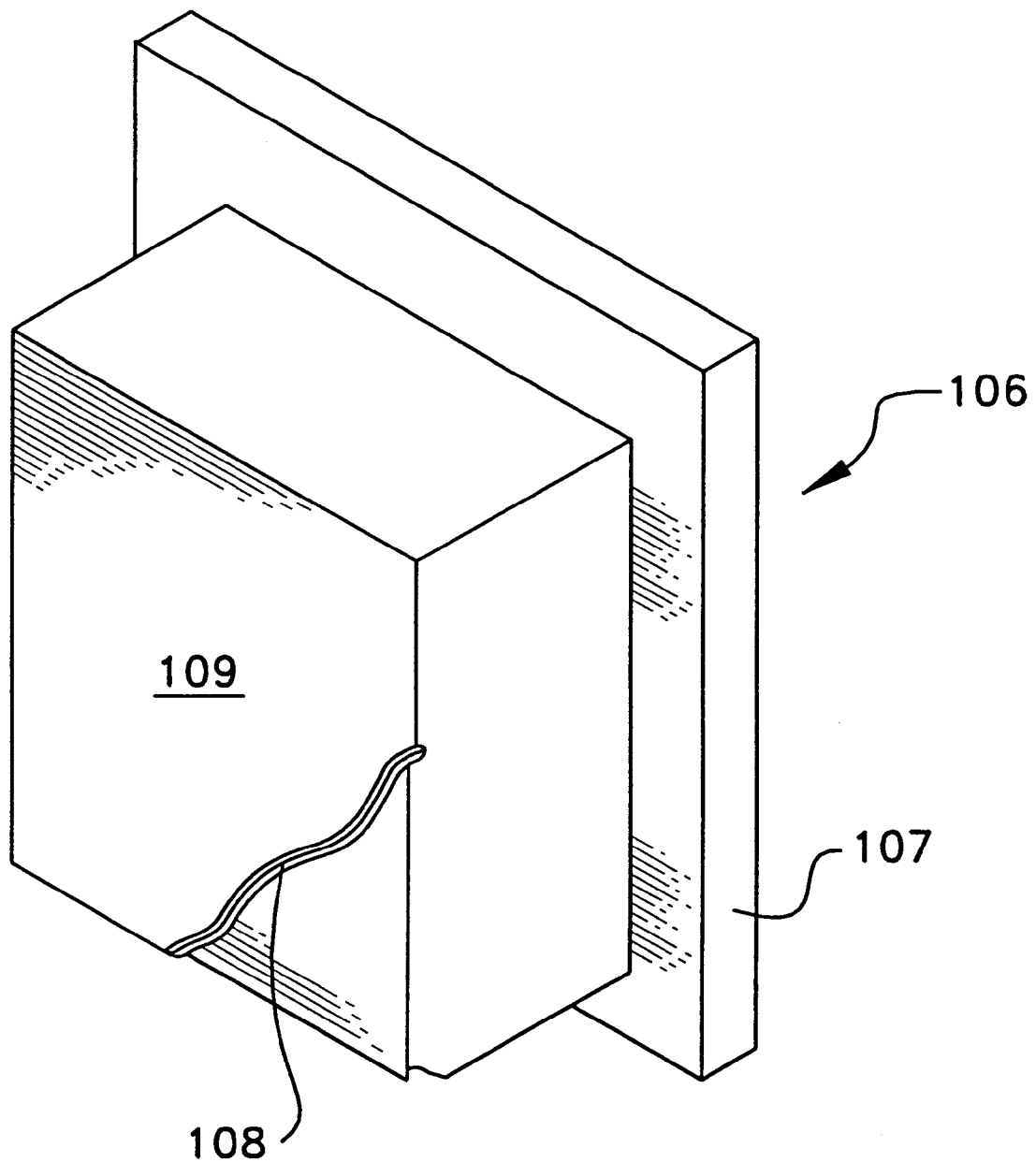
Figure 10A:
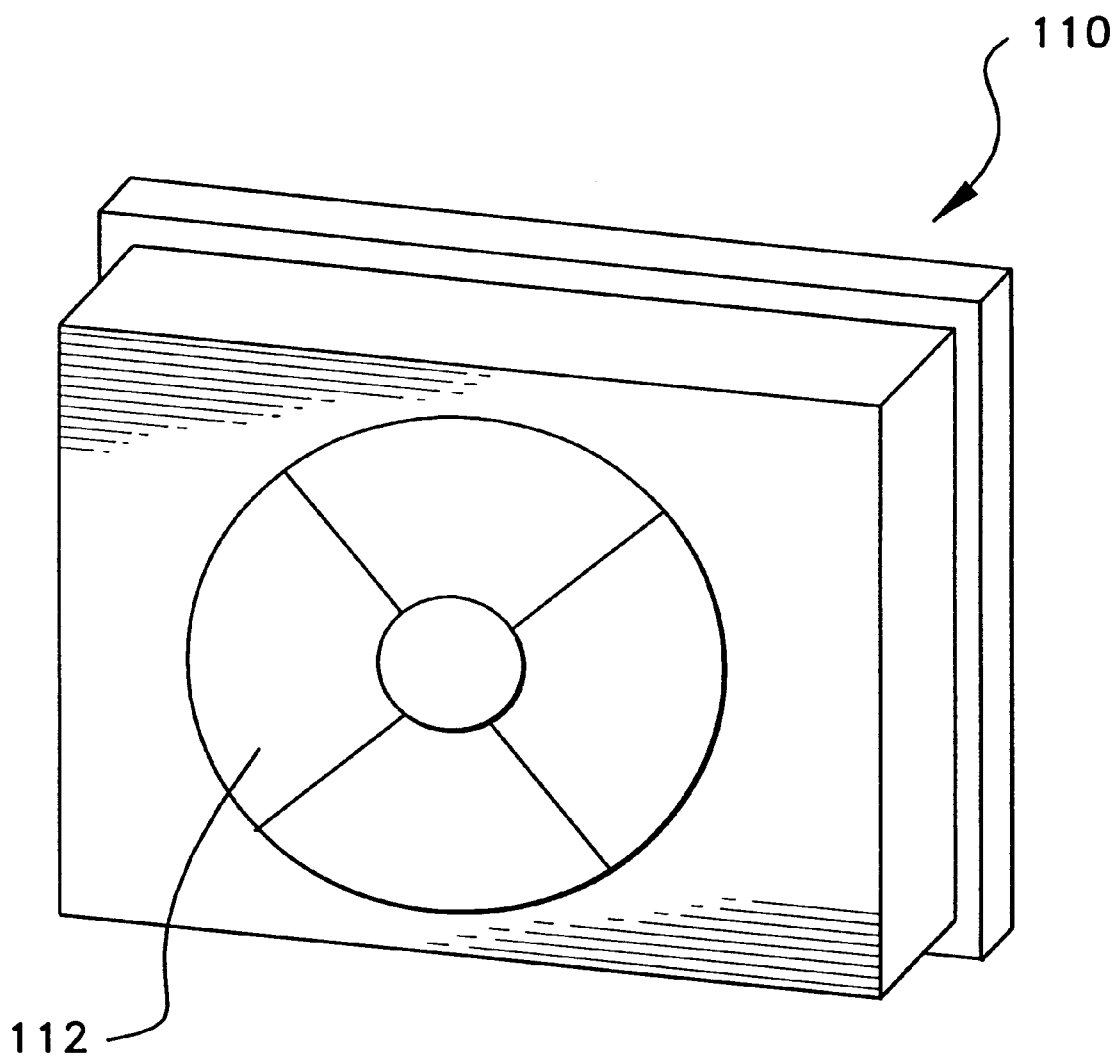
Figure 10B:
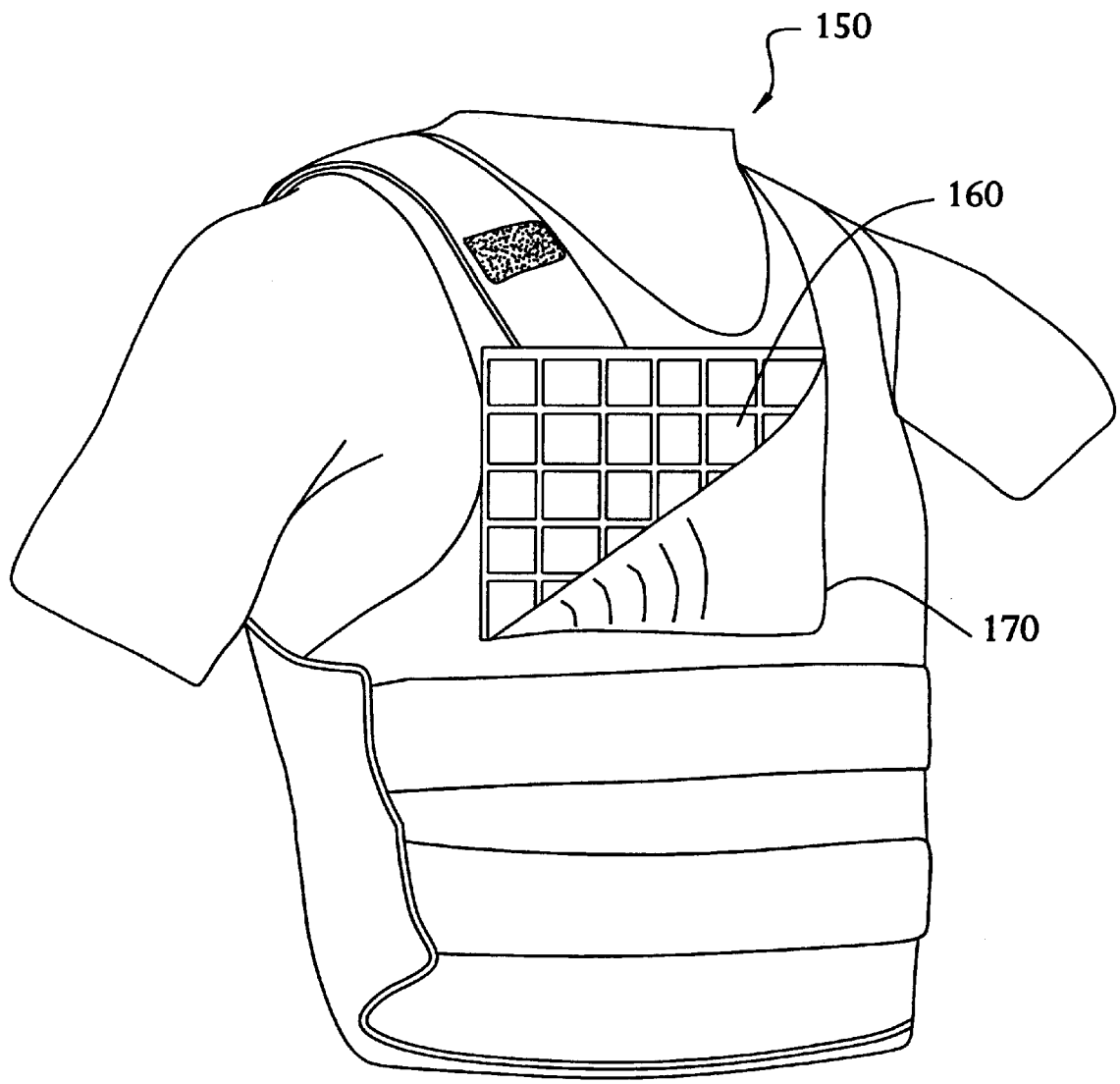
Figure 11:
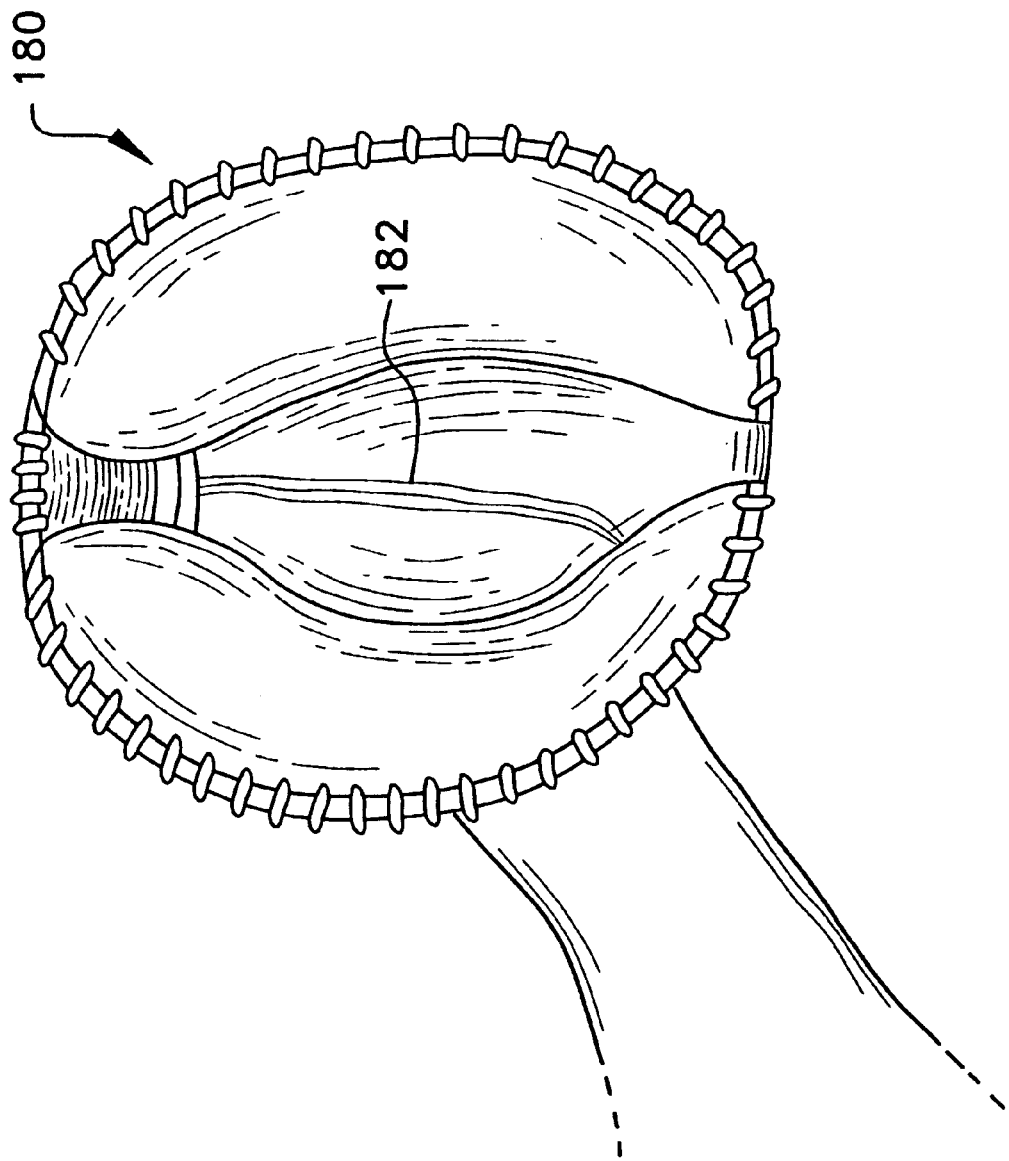
Figure 12:
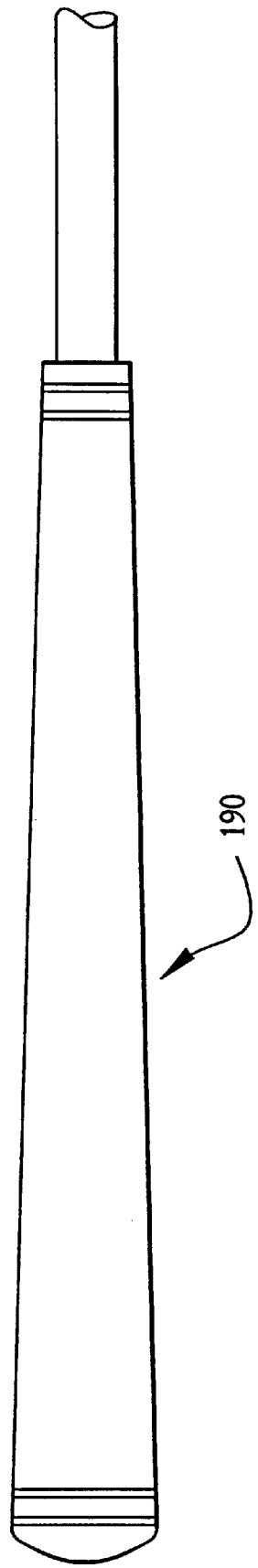
Figure 13:
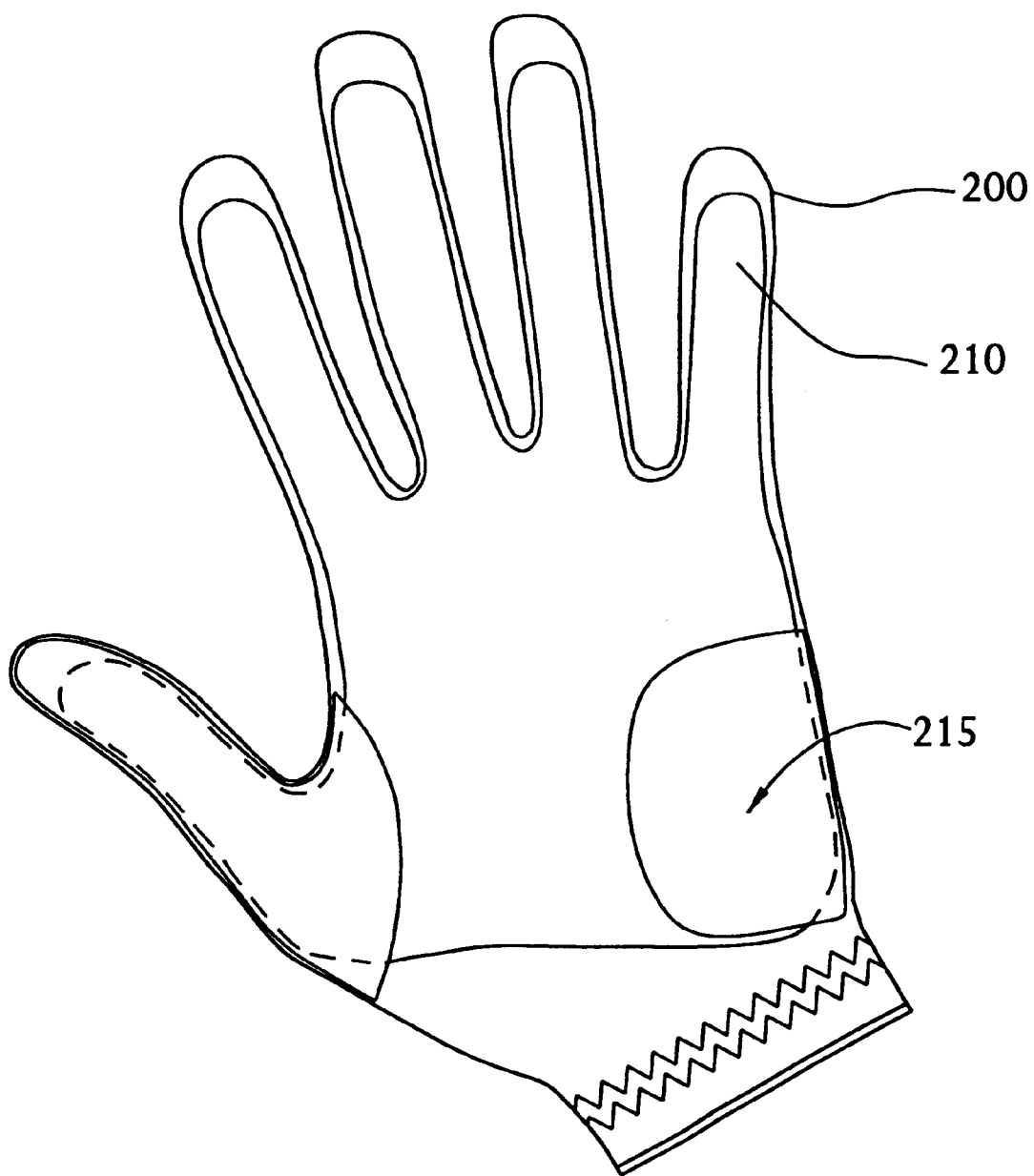

The accompanying drawings illustrate preferred embodiments of the invention according to the practical application of the principles thereof, and in which:

FIG. 1: is an exploded perspective view of the capacitive sensor construction of the present invention;

FIG. 2a: is an exploded perspective view of the capacitive sensor construction of the present invention in a three layer configuration;

FIG. 2b: is a circuit representation of the capacitive sensor construction of the present invention in a three layer configuration;

FIG. 3: is a diagram of a driven shield circuit;

FIG. 4a: is a diagram of an analog conversion circuit incorporating the teachings of the present invention;

FIG. 4b: is a diagram of an output signal corresponding to circuit 4a;

FIG. 5a: is a diagram of a digital conversion circuit incorporating the teachings of the present invention;

FIG. 5b: is a diagram of an output signal corresponding to circuit 5a;

FIG. 6: is a diagram of a microprocessor controlled circuit incorporating the teachings of the present invention;

FIG. 7: is a perspective view of a squeeze ball embodiment incorporating the capacitive sensor of the present invention;

FIG. 8: is a perspective view of a grip cylinder embodiment incorporating the capacitive sensor of the present invention;

FIG. 9: is a perspective view of a striking board embodiment incorporating the capacitive sensor of the present invention;

FIG. 10a: is a perspective view of a striking board embodiment incorporating a plurality of capacitive sensors of the present invention;

FIG. 10b: is a perspective view of a striking vest incorporating a plurality of capacitive sensors of the present invention;

FIG. 11: is a perspective view of a baseball glove embodiment incorporating the capacitive sensor of the present invention;

FIG. 12: is a perspective view of a golf grip embodiment incorporating the capacitive sensor of the present invention; and FIG. 13: is a perspective view of a golf glove embodiment incorporating the capacitive sensor of the present invention.

A DETAILED DESCRIPTION OF THE INVENTION

The preferred embodiment will be described with reference to the drawing figures where like numerals represent like elements throughout.

Referring to FIG. 1, there is shown a capacitive sensor 1 made in accordance with the teachings of the present invention. The capacitive sensor 1 is shown consisting of an open cell polyurethane foam dielectric 10 sandwiched between two conductor layers 12 and 14, respectively. Two end plates 16 and 18 fully enclose the sandwiched layers.

FIG. 2a shows an alternate embodiment of the capacitive transducer in a three layer configuration. The sensor 20 is comprised of foam dielectric layers 22 and 24 surrounded by conductor layers 30, 32 and 34 in alternating fashion. As in the two layer construction shown in FIG. 1, two end plates 36 and 38 fully enclose the sandwiched layers.

Referring to FIG. 2b, there is shown a diagrammatic representation of the three layer capacitive force sensor. The sensor is comprised of a plurality of dielectric layers 42, layered with conductive plates 40. Two end plate insulators 48 fully enclose the dielectric and conductive plate layers. In essence, the sensor itself can be thought of as a variable capacitor, as represented by 46, i.e., one element in a circuit such as an astable multivibrator circuit where the output square wave varies in frequency as the capacitance changes, as shown in the signal of FIG. 5b, (denoted as signal 1). As designated by reference number 44, this three conductor capacitive force sensor is substantially equivalent to the circuit representation of a capacitor, as designated by 46. The capacitive sensor could also be one element in a circuit such as a continuously triggered monostable multivibrator circuit where the output square wave varies in duty cycle as the capacitance changes, as shown in the signal of FIG. 4b, (denoted as signal 2). This square wave could then be input into a low pass filter so as to make it a DC voltage.

The sensor as a component in a fully analog circuit can be implemented in a variety of manners to produce responses in the form of sound, vibration and light. To vary sound frequency with respect to force, the signal from the circuit shown in FIG. 5a, signal 1 shown in FIG. 5b, could be simply fed through an amplifier to a speaker. Alternatively, the DC component of signal 2 which is shown in FIG. 4b, could control a voltage controlled oscillator whose variable frequency output is then fed through an amplifier to a speaker. To vary sound intensity with respect to force, the DC component of signal 2 could be fed directly to a set frequency piezoelectric buzzer.

With respect to vibration, signal 1 (variable frequency), signal 2 (variable duty cycle) or the DC component of signal 2 could act as input signals to a motor driving circuit that would vary the speed of a motor attached to a non-balanced weight, thereby effectively changing vibration intensity.

Finally, with respect to light, the DC component of signal 2, could be directly fed to a light to change its intensity. The component of signal 2 could also be fed to a series of comparators whose other input is from a voltage divider circuit. The output of these comparators could then be connected to multiple lights so that more or less lights are lighted as capacitance increases. This circuit would be similar in some respects to an LED bar graph.

The inclusion of digital components, such as, but not limited to, a microprocessor, a sound chip, digital-to-analog and analog-to-digital converters, LED/LCD controllers and displays, and logic chips, greatly expands the possibilities whereas an applied force is sensed which leads to some form of response that may be sound, vibration, or light. One example is shown in the circuit of FIG. 6 where a digital readout of the applied force is made possible by inclusion of a microprocessor, LCD drivers, LCD display and piezoelectric buzzer.

A motion detection circuit could be a part of any of the herein referenced circuits so that when the item is shaken it turns itself on automatically. To conserve battery power, their may exist some type of timer circuit (e.g., a capacitive decay circuit) that eventually turns the unit off if it is not being used. This could be used in either the manual (switch) or automatic (motion detector) power up embodiments.

In operation, when first turned on, either by turning on a power switch or by shaking the device in the case of it having a motion detection circuit, there would ideally be a short signal that acts as notification of the power being turned on. This signal could be a sound, a vibration or a light. After that initial signal the device should probably be in a pseudo-sleep mode if there is no force applied so as to conserve power. As force is applied a multitude of responses in terms of sound, vibration or light could be provided. For example, Sound: A sound would be emitted that either varies in frequency or intensity (frequency being constant); Vibration: A vibration could be initiated that varies in intensity; Light: A single light could vary in intensity, or if there are multiple light sources, vary in the number of lighted sources. Combinations: Various combinations of sound, vibration and light could also be possible. Threshold: A sound, vibration or light could also be produced only if force is applied above a certain threshold.

In addition, different sensitivity levels could be incorporated depending upon the force generating ability of the user, e.g. higher sensitivity ratings for younger children and lower sensitivity ranges for young teenagers.

Referring now to FIG. 3, there is shown a circuit diagram for the implementation of a driven shield in the present invention. Referring back now to FIG. 2a the sensor as implemented in accordance with the teachings herein would have conductor layer 34 correspond to connection 52; conductor layer 32 correspond to connection 50; and conductor layer 30 correspond to connection 58. One disadvantage to any capacitive force transducer is that it can be effected by electromagnetic fields (EMF), static, etc. A driven shield is one way to reduce this interference ("active shielding"). The 3-layer capacitor is shown in FIG. 2a another way ("passive shielding"). In regard to the "active shielding" method and the driven shield circuit shown in FIG. 3, one steel mesh layer is represented by 50 and the other is represented by 58. Another layer of steel mesh is represented by 52 which is properly grounded. Element 54 is an ordinary linear operational amplifier and element 56 is the feedback connection for this voltage follower circuit.

The driven shield provides for significant noise reduction in the capacitive sensor. With respect to FIG. 2b, the open cell polyurethane foam layer represented by 22 will be replaced with a thin non-compressible material layer such as vinyl or paper instead of a polyurethane foam.

As discussed, representative capacitance conversion circuit for the sensor in both analog and digital form, respectively, are shown in FIGS. 4a and 5a. The circuit of FIG. 5a as represented by 60, provides for a pulse train of variable frequency as indicated by arrow 62 and shown as signal 1 in FIG. 5b. The signal has a period represented by 64. Frequency is represented by the following equation: $f=1/T$ where the frequency, f, is proportional to 1/capacitance of the sensor. As shown the pulse generator 80 is an astable multivibrator having a variable output frequency pulse train.

As shown in FIG. 5b, the circuit is represented by 66, which provides a pulse train of constant frequency with a variable duty cycle as indicated by arrow 68 and shown as signal 2 in FIG. 4b. In this circuit, the period is represented by 74 which is a summation of $t_1$ as represented by 70 and $t_2$ as represented by 72, where $t_1$ is proportional to the capacitance of the sensor. As shown, a pulse generator 90 is an astable multivibrator of constant frequency and is connected as represented by line 92 to a capacitance to duty cycle converter 94 which in the preferred embodiment is a continuously triggered (by 92) monostable multivibrator.

In construction of the multi-layer sensor disclosed herein, the conductors are made of wire mesh, similar in appearance to window screen. In the three conductive layer sensor, both outer conductors are grounded and thus are less subject to noise than the two conductive layer sensor. The sensor could be polyurethane, neoprene, or other compressive material. The conductor could be a wire mesh (e.g., screen); bare wire wrapped around many, many times (similar in construction to a baseball); metallized fabric (Flectron® is used now); a conductive elastomer (e.g., conductive silicon rubber) in either sheet, paste or spray on form; a conductive adhesive; standard foil; or a conductive paint that is applied either by brush, spray or dipping.

Although nearly any compressible material may be used as the dielectric, the preferable material is polyurethane foam. The preferred polyurethane foam is characterized in terms of chemistry, density, firmness and morphology. Chemically, polyurethanes are formed as diisocyanates (having the general structure R--N==C==O) react with polyols (alcohols). Density is commonly referred to as pounds per cubic foot, or pcf. The preferred density range for the present invention is 5–50 pcf. Firmness, is defined as the compressive force (expressed as pounds per square inch, or psi) required to cause a 25% compression of the polyurethane foam. (A device causing a 0.2 inch/minute strain rate is used). The preferred firmness range for the instant invention is 0.1–100 psi. Morphologically, the foam is made up of a plethora of approximately spherical cells. The preferred average cell diameter is 50–200 microns. Cells are in communication through a multitude of pores (thus, "open cell"). Unimpeded air flow through the foam substance helps established resilience. On formal testing there is a loss of 5% thickness or less on an ASTM 1667 compression set at 73 degrees Fahrenheit. Foams of this type are preferably manufactured by Rogers Corp., Poron Materials Divisions, East Woodstock, Conn.

Polyurethane (unlike other open-cell foams) has been well-known in the field of rehabilitation medicine for several years. The conventional application is as foam padding for protective use in shoes. Although well known, no one has thought to incorporate it into a force transducer. The same features that make it a good protective foam cushion with excellent energy absorptive properties also make it the best available capacitive dielectric. These include unsurpassed resiliency to both static and dynamic loading, and linearity with compression.

Polyurethane was found superior to neoprene and polyethylene foams in resiliency on extensive dynamic testing when shaped as a shoe insole and inserted into shoes (Brodsky, et. al., Foot and Ankle, Vol. 9, December 1988, pp. 111–116). Polyurethane showed no loss of thickness for 10,000 cycles of compression or shear compression. (10,000 cycles corresponds to 9 hours of walking at normal cadence), whereas neoprene showed a 5–15% loss of thickness, and polyethylene showed a 15–50% loss of thickness. Devices made with polyurethane should thus last a very long time. Further, one expects devices made with polyurethane be far more durable than those constructed with polyethylene or neoprene foams.

Furthermore, testing reveals polyurethane to have far better resiliency to static loading than polyethylene and neoprene foams. A square of polyurethane may be placed under a desk leg for a week and return immediately to its original shape. However, neoprene or polyethylene foams would remain permanently compressed.

The second advantage of polyurethane is improved linearity with compression. It is fortuitous but gratifying that this sensor is linear within narrow limits from zero to 75% compression of the dielectric. The range of linearity of pressure to compression is wider than the other two foam materials. Thus, non-uniform loading conditions where there are localized areas at different levels of compression should yield equivalent capacitance change to a more uniform load.

Additionally, creep is imperceptible with greater than 75% compression for extended periods. This is in contrast to neoprene and polyethylene foams, which show significant creep at this level of compression In construction, the final sealing layers (i.e., the end plates) as described herein can be constructed of a variety of flexible or rigid materials including vinyl, polyurethane film, plastic, or rubber. The layers can also be treated with selective hydrophilic or hydrophobic coatings for directing or repelling water, as desired.

A number of illustrative samples incorporating the capacitive sensor disclosed here are disclosed herein for exemplary purposes only. In no way should the following examples be considered exclusive but are merely included herein for the purpose of demonstrating the flexibility of the present invention.

EXAMPLE 1

A Squeeze Ball (non-microprocessor, analog):

The squeeze ball has been most notably used as an excellent toy available at point-of-purchase stands at drug stores, supermarkets etc. The squeeze ball has also been shown as an effective device to relieve stress and tension, reduce pain and stiffness due to arthritis or hand fatigue, lower blood pressure, increase strength and dexterity in your fingers, hand, wrists and arms. The squeeze ball can be used for anyone including health care professionals, athletes, office personnel, arthritis sufferers, computer users, etc. The squeeze ball can also be used for merely recreational purposes, such as for a toy.

Construction: A squeeze ball 120 incorporating the teachings of the present invention is shown in FIG. 7. The main structural component is a hollow, spherical ball that could be of various wall thickness and of variable diameter, preferably 1"–4" in diameter. Around the shell would be either a two layer or three layer capacitor as previously described. The three layer is preferable in this embodiment since both outer conductors are grounded and thus are less subject to noise than two layer materials. Although polyurethane as the dielectric would lead to a more reliable product. The dielectric could be polyurethane, neoprene, or other compressive material. The conductor could be a wire mesh (e.g., screen); bare wire wrapped around many, many times (similar in construction to a baseball); metallized fabric (Flectron® is used now); a conductive elastomer (e.g., conductive silicon rubber) in either sheet, paste or spray on form; a conductive adhesive; standard foil; or a conductive paint that is applied either by brush, spray or dipping.

By adjusting the Young's modulus and or the thickness of the foam (the ease of compressibility), harder and softer squeeze balls could be made. In particular, by adjusting the density and particular formulation of the foam, the hardness/softness of the squeeze ball can be varied.

If not intended to be a throw-away novelty then there must also exist some type of battery holder and cover built into the shell. If the device is to be turned on manually (rather than automatically upon shaking the device) then there must also exist some type of switch incorporated into the shell. This switch would allow the user to switch between a predetermined set of force ranges. Wires that attach to the internal electronics will feed through the ball and attach to the conductive layers of the sensor as these layers are added. The electronics would fit in groves or on mounts inside the shell and be either glued or screwed into place securely. The circuit for this squeeze ball could be those shown in FIGS. 4a and 5a as discussed above.

This squeeze ball embodiment must not necessarily be spherical. It could be egg shaped or even cylindrical, as illustrated in FIG. 8, by cylindrical squeeze ball 122, for instance. It could also be more ergonomic in design, having indents in which the fingers are supposed to be placed.

Operation: The squeeze ball would be turned on be either shaking the ball or by activating its power switch. Upon power up there would ideally be a short signal that acts as notification of the power being turned on. This signal could be a sound, a vibration or a light. In operation, the squeeze ball would react to a variable force by a variety of means including sound, vibration, light or any combination of these.

EXAMPLE 2

A Squeeze Ball (microprocessor):

Construction: The construction is essentially identical to the non-microprocessor controlled squeeze ball as described above, although with different circuitry as described below. The circuit would include that described above, but with the addition of a microprocessor that would measure the applied force either by using an algorithm that determines the frequency from signal 1 of the circuit shown in FIG. 5a, or by determining the pulse width of signal 2 from the circuit shown in FIG. 4a or by converting signal 3, the DC component of signal 2, to a digital number. In either case the calculated variable is a measure of the applied force, and this number would be used in other algorithms to determine the toys output signal which could be sound, vibration, light or any combination of these. The inclusion of a microprocessor greatly increases the capabilities of such a toy. All of the outputs as described in the Operation section of the non-microprocessor would still be available and more easily controlled with potentially fewer components, especially for combination effects. A sound chip could be easily included and controlled by the microprocessor. A memory chip could also be included that could record usage and change the output characteristics of the device over time. For example, if some game algorithm were programmed in the microprocessor then the device could progressively become more challenging to the player over time.

for signal 1, the period (1/frequency) is proportional to capacitance, an algorithm basically causes the processor to sit there and count clock cycles from rising edge to rising edge (one whole period). This can actually be performed many times with an average taken so as to reduce the effects of noise. It really is the number of clock cycles that is proportional to capacitance. This number is used below.

for signal 2, the on time of the pulse is proportional to capacitance, an algorithm basically causes the processor to sit there and count clock cycles from rising edge to falling edge (time high). This can actually be performed many times with an average taken so as to reduce the effects of noise. It really is the number of clock cycles that is proportional to capacitance. This number is used below.

for signal 3, one of the standard methods for analog-to-digital conversion is used, e.g., single-ramp integrating, double-ramp integrating, single counter, tracking or successive approximation. This number is used below.

from that number: force=$A+B*_{(1/C)}$ where A and B are calibration constants (assumes linearity) and C is determined above.

from the number: force=$A+\Sigma_{i=1}$ to N $\{B_i*(1/C)^i\}$ where A and $B_i$ are calibration constants and N is an integer, this does not assume linearity and will be more accurate since it makes corrections for curvilinear behavior. C is the number determined as described above.

Operation: When first turned on there would be a power-on notification signal similar to the one for the non-microprocessor based squeeze ball as described above. Operation of the device is dependent upon the microprocessor algorithm installed. (1) It could be programmed to behave exactly like the non-microprocessor device described above. (2) With the inclusion of a sound chip, it could emit different sounds or voices at various applied forces. For instance, if a light force were applied, the ball could be programmed to say, "You wimp!"; if a medium force were applied it could say, "So you think you're tough, huh?", and if a stronger force were applied it could say, "Ouch, I give up, you win!" Other sounds, vibrations and lights could also be initiated at these various force levels. (3) With the inclusion of some memory storage device, games could be played where the user has to follow certain instructions in order to ultimately win the game. For instance, there could be a force matching game where the device gives a signal, such as a sound, and the user has to match that exactly before progressing to the next level. (4) The device could be used for a strength competition game between children to see who is the strongest. In such an instance the number of players could be selected by adjusting a "player number" knob or switch or by initially squeezing the ball a certain number of times to denote the number of players. Each player in turn would squeeze the ball, which may or may not emit a feedback signal that is a measure of the applied force, and after every player had their turn the device would announce the winner through appropriate sound, light or vibration responses.

EXAMPLE 3

Interactive Dolls and Plushes:

Construction: For a doll that is made out of hard plastic or hard rubber the sensor could be wrapped around the outside of the body. Wires from the sensor would attach to a circuit module that would be internal to the doll. For plushes (e.g., stuffed animals) the sensor would more likely be wrapped around a spherical, cylindrical or cubical module that would be stuffed into the plush. The circuit for this module that would be inside the module itself. With respect to the circuit it could be exactly the same as those described for the microprocessor or non-microprocessor squeeze balls described above. In a preferred embodiment of the interactive doll, a power switch, skill switch and player number switch could be incorporated.

Operation: The operation of the this embodiment could be exactly the same as those described for the microprocessor and non-microprocessor squeeze balls described above.

EXAMPLE 4

Impact Toys:

Construction: The sensor as disclosed herein could be wrapped around or otherwise placed on objects that are intended to strike other objects (e.g., a bat or paddle). The sensor described could alternatively be inserted or placed on objects that are themselves hit or struck in some fashion (e.g., as shown in FIG. 11, inside a catchers mitt 180 or inside a striking pad). It is contemplated that the object on which the sensor is attached could be anything, including existing products that can be modified or new product concepts. The sensor 182 is attached to a circuit that is either inside the object or somehow mounted outside the object.

The circuit will more than likely contain some type of microprocessor similar to that described above. A digital readout or an LED/LCD bar graph with associated driving circuitry could be present to display the impact force. A sound chip could also be present so that different sounds could be emitted from the device depending upon the amount of impact force.

Operation: The operation of the device would depend upon what type of impact was made. For example, if the sensor lined a catcher's mitt it may say, "That was smoking'!" if the caught ball was especially fast. A digital readout of the force could be attached to the mitt for the catcher or thrower to see. If the sensor was placed in a pad that was struck in some fashion a readout of the impact force would seem logical. In this case the numbers could reset themselves to zero automatically after a set amount of time. Another mode of operation for the striking pad is that the device could prompt the player when to strike. When the player does so, a readout of the time required to strike a pad, the reaction time, could then be displayed.

EXAMPLE 5

Impact Sports (martial arts):

The sensor could be incorporated in Makiwaras, hand held and wall mounted targets and shields, heavy bags, vests for sparring, hand and foot pads, head gear. Referring to FIGS. 9 and 10a, a striking board 106 or Makiwara is shown. The Makiwara is a punching board typically used to toughen the hands and giving training in hand, elbow and foot striking techniques. Regular use of makiwara will develop strong technique, rather than techniques that are thrown into the empty air. It gives practice in focusing, muscular control, breath control and is a convenient way to toughen the skin of the knuckles and other striking points. Because it is difficult to master the technique of focus (concentration of strength at the moment of impact), many martial arts experts feel that the techniques of those who don't use the makiwara (or other target, for that matter) are bound to lack power.

Construction: Typically the makiwara consists of a straight board 107 with the top portion 109 fitted for punching. Commercially available makiwara are typically ½"–1" thick board with approximate dimensions of 4"×12" or 12"×12". Traditionally, the striking surface of the makiwaras consisted of a bundle of straw with rope tightly wound around it at the top part of the board for about one foot. More recently, a piece of sponge rubber, typically about two inches thick, four inches wide and one foot long, covered with canvas has been widely used. But anything that cushions the shock of impact can be used.

For implementation purposes, one sensor 108 as disclosed herein should suffice for basic force measuring applications. However, where accuracy is crucial, a target 110 can be constructed of a variety of separate and distinct sensors 112 (such as shown in FIG. 10a), each measuring a certain area of the target surface. Another similar embodiment would be a sparring vest 150 that could be worn by the participants, as shown in FIG. 10b. Constructed of a plurality of discrete sensors 160, the vest could record and display the force and location of impact. The vest has a removable flap 170 to cover the sensors 160. Such a vest would be used for training and competition purposes.

Additionally, a related implementation could be a board breaking simulation device that you hold for breaking (10"×12") but is unbreakable. The device could provide a readout in terms of boards or cement blocks that would have been broken based upon already established force relations.

Operation: Other operational modes could be similar to those described for impact toys above.

EXAMPLE 6

Golf Grip:

In playing golf, it is important to know pressure of the grip during swing. Excessive gripping of the club at the peak of the swing is a serious problem among golfers. The sensor could be built around the grip handle, in the form of a zipper or condom for portability or could be incorporated into a golfing glove.

Construction: A golf grip 190 incorporating the teachings of the present invention is shown in FIG. 12. The glove 200 includes a sensor element 210 and additional padding 215. The three layer capacitive sensor is preferable in this embodiment since both outer conductors are grounded and thus are less subject to noise than two layer materials.

Operation: The operation of the golf grip would respond to the pressure of the golfer's hands. For example, the sensor may be connected to a device such as a LED light or buzzer which would signal if too much pressure was being applied to the club.

OTHER EXAMPLES

1. Golf Application/Swing impact: As an extremely rugged sensor, it could be built into the club head, where it would give a readout of force impulse or energy of the swing against the ball. This feedback might improve impact efficiency not only through force of follow though, but aligning the club with the ball so that the golfer always contacts the "sweet spot".

2. Wound healing: A compression bandage is an often used technique for treating lower extremity skin ulcers (wounds) caused by venous insufficiency. In these case, a sterile dressing is applied directly over the wound, and an elastic wrap that is approximately four inches wide and ten to twenty feet long is wrapped circumferentially around the lower leg, from ankle to knee. It is important to maintain enough compressive force to reduce edema (swelling) but not so much so that circulation is inhibited. A sensor incorporating the teaching of the present embodiment could be applied to the leg prior to wrapping the elastic wrap. A circuit attached to the sensor would display the compressive force so that the person doing the wrapping can determine if his or her technique is correct.

3. "Smart shoe insoles," a biofeedback or diagnostic device: The insole would have islands for the seven major pressure areas under the foot, the great toe, the five metatarsal heads and the heel. There would be different sizes that would fit into standard shoes. An electronics module would fit around an extension of the insole on the lateral side of the shoe. Which island that is active may be preselected easily. If the threshold normal force exceeds 10 kg/cm$^2$, the shoe would begin to beep or provide some alternate feedback. As a diagnostic tool, the force of each island could be recorded or alternatively be transmitted via telemetry to a base station. A therapist could then make a diagnosis upon comparison with normative data.

4. "Smart mattress pad", turn patient reminder: A mattress pad incorporating the cap sensor of the present invention can be an attachment to a hospital bed. It could be a separate item that is attached to the bed by straps under the mattress. It does not need to be from head to toe, but could be from shoulder or mid thorax to thigh. The system could detect if there was relative compression change of these sensor elements consistent with turning patient from side to side. If not, it could cause an alarm to emit so that the nursing staff could do the requisite side to side turns, typically every two hours. It is a quality assurance measure to cut down the frequency of pressure ulcers in nursing homes, a very significant problem. The system could come with a incontinence shield, e.g., a rubber coating, that is impervious to body secretion, such as blood, urine and feces. It would be relatively inexpensive, reliable and long lasting. It could be battery powered for home use. However, since most hospital beds do use AC power, the required circuitry could be driven off this supply after it is converted to a usable DC source. Alternatively, it could be built into a mattress for license to a company that manufactures and markets these products.

5. Stretch Sensor: In this embodiment, the preferred construction would utilize therabands. By way of background, therabands are flexible rubber strips of variable and selectable stiffness. One can stretch the theraband by grasping the ends with the two hands in a continuous motion; movement exercise against resistance is termed isotonic exercise.

Almost any muscle of the extremities can be strengthened isotonically by proper positioning and orienting the theraband. An example of isotonic exercise with the theraband is grasping it with both hands in front of the body and spreading horizontally, to strengthen trapezium, or vertically to strengthen deltoid (top arm) and latissimus dorsi (bottom arm). Therabands are color coded by stiffness, so one graduates from less stiff to more stiff exercisers. Therabands are inexpensive, portable and rugged, so are ideal for home isotonic exercise.

However, feedback of performance is limited because there is no readout of force, other than the wide force range that color delimits. In order to supply this feedback of performance, manufacturers are now developing therabands with strain gauges attached to read out force and supply feedback of performance. However, feedback using a strain gauge is very costly, i.e. a unit may cost several hundred dollars. There are drawbacks of other sensor types; springs are bulky, unattractive or possibly dangerous. Other sensor types are not elastic. These include resistive sensors, switches, hydraulic or piezoelectric elements.

Unlike these prior art sensor types, stretching exercise force can easily measured by an elastic capacitive sensor. This capacitive sensor can be sewn onto the theraband and stretch along with it. With stretch, the capacitive sensor increases in area and becomes thinner. By both thinning and expanding in area, capacitance increases with stretch.

The best possible capacitive stretch sensor is the force sensing fabric because it will not wear out: By definition, it always returns to its original area and thickness after being stretched. This stretch sensor architecture is similar to other embodiments of the force sensing fabric. However, the sensor has elastic conductors in the direction of stretch.

The sensor performance, though probably non-linear, can be linearized by simple electronics that converts capacitance to force by an internal look up table. This conversion electronics will be self contained in a tiny package. This package is attached to the feedback element which could be LCDs, sounds or lights. This adds enjoyment and builds commitment to isotonic exercise. Increased motivation improves strength and fitness.

While the present invention has been described in terms of the preferred embodiment, other variations which are within the scope of the invention as outlined in the claims will be apparent to those skilled in the art.

What is claimed is:

1. A multi-layer capacitive sensor comprising:
   a plurality of layers forming a force sensing detector, the layers including dielectric and conductive portions;
   circuitry for providing feedback in response to a signal from the force sensing detector; and
   a housing encompassing the force sensing detector and said circuitry.

2. The sensor of claim 1 wherein the housing is a squeeze ball.

3. The sensor of claim 2 further comprising:
   a microprocessor for measuring the applied force by the user to the ball.

4. The sensor of claim 2 further comprising:
   analog devices for measuring the applied force by the user to the ball.

5. The sensor of claim 1 wherein the housing is a squeezable device.

6. The sensor of claim 5 wherein the circuitry is analog.

7. The sensor of claim 5 wherein the circuitry is digital.

8. The sensor of claim 1 wherein the housing is a hitting target.

9. The sensor of claim 1 wherein the housing is an impact vest.

10. The sensor of claim 1 wherein the housing is a baseball glove.

11. The sensor of claim 1 wherein the housing is a golf grip.

12. The sensor of claim 1 wherein the housing is a golf glove.

13. The sensor of claim 1 wherein the housing is a compression bandage.

14. The sensor of claim 1 wherein the housing is a foot insole.

15. The sensor of claim 1 wherein the housing is a mattress pad.

16. The sensor of claim 1 further comprising an enclosure for protection of the circuitry.

17. The sensor of claim 1 further comprising a switch integral with the sensor for selecting different levels of sensitivity for the sensor.

18. The sensor of claim 1 further comprising elastic conductors.

19. A moldable capacitive force sensor comprising:
   a plurality of layers forming a force sensing detector, the detector providing an output signal in response to pressure;
   circuitry for providing feedback in response to the output signal from the force sensing detector; and
   a housing encompassing the force sensing detector and the feedback providing means.

20. The sensor of claim 19 wherein the housing is a squeeze ball.

21. The sensor of claim 19 wherein the housing is a squeezable device.

22. The sensor of claim 19 wherein the housing is a hitting target.

23. The sensor of claim 19 wherein the housing is a baseball glove.

24. The sensor of claim 19 wherein the housing is a golf grip.

25. The sensor of claim 19 wherein the housing is a golf glove.

26. The sensor of claim 19 wherein the housing is an impact vest.

27. The sensor of claim 19 wherein the housing is a compression bandage.

28. The sensor of claim 19 wherein the housing is a foot insole.

29. The sensor of claim 19 wherein the housing is a mattress pad.

30. The sensor of claim 19 further comprising a protective encasement for protection of the circuitry.

31. The sensor of claim 19 further comprising a switch integral with the sensor for selecting different levels of sensitivity for the sensor.

32. The sensor of claim 19 further comprising elastic conductors.

33. A capacitive sensor in a three-layer configuration comprising:
   three conductor layers alternating with foam dielectric layers;
   a pair of end plates for enclosing the foam dielectric and conductor layers; and
   circuitry electrically connected to the conductor layers for providing feedback from the sensor.

34. The sensor of claim 33 further comprising a protective encasement for protection of the circuitry.

35. The sensor of claim 33 further comprising a switch integral with the sensor for selecting different levels of sensitivity for the sensor.

36. The sensor of claim 33 wherein the sensor is incorporated into a squeeze ball.

37. The sensor of claim 33 wherein the sensor is incorporated into a squeeze cylinder.

38. The sensor of claim 33 wherein the sensor is incorporated into a hitting target.

39. The sensor of claim 33 wherein the sensor is incorporated into a baseball glove.

40. The sensor of claim 33 wherein the sensor is incorporated into a golf grip.

41. The sensor of claim 33 further comprising elastic conductors.

* * * * *